(12) United States Patent
Alghamdi et al.

(10) Patent No.: US 9,192,301 B2
(45) Date of Patent: Nov. 24, 2015

(54) RADIOLOGICAL SIMULATION

(75) Inventors: Ali Alghamdi, Dammam (SA); Andy K. W. Ma, Dammam (SA)

(73) Assignee: Masar Scientific UK Limited, Guildford (GB)

(*) Notice: Subject to any disclaimer, the term of this patent is extended or adjusted under 35 U.S.C. 154(b) by 232 days.

(21) Appl. No.: 13/988,004

(22) PCT Filed: Nov. 18, 2011

(86) PCT No.: PCT/GB2011/052268
§ 371 (c)(1),
(2), (4) Date: Aug. 17, 2013

(87) PCT Pub. No.: WO2012/066351
PCT Pub. Date: May 24, 2012

(65) Prior Publication Data
US 2013/0329982 A1 Dec. 12, 2013

(30) Foreign Application Priority Data
Nov. 18, 2010 (GB) .................................. 1019533.7

(51) Int. Cl.
G06K 9/00 (2006.01)
A61B 5/00 (2006.01)
G06F 19/00 (2011.01)
G09B 23/28 (2006.01)

(52) U.S. Cl.
CPC .......... *A61B 5/0033* (2013.01); *G06F 19/3437* (2013.01); *G09B 23/286* (2013.01)

(58) Field of Classification Search
CPC combination set(s) only.
See application file for complete search history.

(56) References Cited

U.S. PATENT DOCUMENTS

| | | | |
|---|---|---|---|
| 6,697,664 B2* | 2/2004 | Kienzle, III et al. | 600/427 |
| 8,038,614 B2* | 10/2011 | Gobeyn et al. | 600/300 |
| 8,311,791 B1* | 11/2012 | Avisar | 703/11 |
| 8,681,152 B2* | 3/2014 | Kubota et al. | 345/424 |
| 2002/0168618 A1* | 11/2002 | Anderson et al. | 434/262 |
| 2004/0066908 A1* | 4/2004 | Hanke et al. | 378/901 |
| 2008/0193904 A1* | 8/2008 | Santhanam et al. | 434/272 |
| 2009/0305215 A1* | 12/2009 | Wilkins | 434/274 |
| 2010/0179428 A1* | 7/2010 | Pedersen et al. | 600/443 |
| 2013/0047103 A1* | 2/2013 | Avisar | 715/764 |

FOREIGN PATENT DOCUMENTS

WO  WO 2004/029911 A1  4/2004
WO  WO 2009/117419 A2  9/2009

OTHER PUBLICATIONS

Ito, Y. et al., "Robust Generation of High-Quality Unstructured Meshes on Realistic Biomedical Geometry," International Journal for Numerical Methods in Engineering, 2006, pp. 943-973, vol. 65.

(Continued)

*Primary Examiner* — Anand Bhatnagar
(74) *Attorney, Agent, or Firm* — Fenwick & West LLP

(57) ABSTRACT

A data processing apparatus, system and method for simulating radiological imaging of a physical object, comprising: an object model generator configured to generate a data model, wherein the data model comprises data representative of the orientation of the physical object with respect to a frame of reference and simulated composition data; and an image simulator configured to perform a radiological simulation on the data model and generate a simulated radiological image of the physical object.

25 Claims, 9 Drawing Sheets

(56) References Cited

OTHER PUBLICATIONS

Kahn, H., "Research Memorandum: Applications of Monte Carlo," RM-1237-AEC, Apr. 19, 1954, The Rand Corporation, 270 pages.

Klein, O. et al., "Uber di Streuung von Strahlung Durch Freie Elektronen Nach der Neuen Relativistischen Quantendynamik von Dirac," Z F. Phys., Oct. 30, 1928, pp. 853-868, vol. 52 (with English abstract).

Lee, C. et al., "Hybrid Computational Phantoms of the Male and Female Newborn Patient: NURBS-Based Whole-Body Models," Physics in Medicine and Biology, 2007, pp. 3309-3333, vol. 52.

PCT International Search Report for PCT/GB2011/052268, Jul. 2, 2012, 5 pages.

* cited by examiner

RADIOLOGICAL SIMULATION

The present invention relates to a data processing apparatus, method and system for radiological simulation and a program for a computer arranged to implement a method of radiological simulation. In particular, but not exclusively, the present invention relates to an interactive simulation system and method for use in radiological procedure training and research.

In radiological training trainees may undergo a programme of study using radiological imaging systems. Programmes of study are generally followed by examination to ensure that trainees have satisfactorily completed the programme of study and to demonstrate that they are capable of using radiological equipment correctly. Trainees may be expected to demonstrate their understanding of the positioning of an object for an imaging procedure, correct set up of an imaging system and what they would expect to observe in resultant images obtained from the imaging procedure.

In medical radiological training, trainees simulate the imaging procedure in a role play environment. Generally, one trainee will act as a patient and a second trainee will act as the radiologist or radiology technologist. In the role play the trainee "radiologist" assists the trainee "patient" into a proper posture under the imaging equipment. The tutor will then show them a radiological image obtained in real life under similar conditions.

Sensor enabled mannequins or dummies have been developed which can be used in place of a human patient. Based on positional information provided by the sensors, a suitable image indicative of the mannequin's position can be called from a computer based image library. Such a system is relatively simple to implement, however it requires a large number of stored images in the library and such images cannot cover every possible position in which a mannequin may be placed for simulating positioning of a patient.

Such training exercises can have great value for trainees as they can learn about how a patient might feel in a position for an imaging procedure as well as the practicality of various postures or positioning of the patient.

International Patent Application number WO2004/029911 relates to a system and method for medical instruction and describes the use of a virtual patient and multimedia simulations of radiological evaluations. However, this system relies on pre-obtained images to represent the virtual patient and the training experience is also limited by the availability of suitably relevant images for a particular patient position or type of evaluation.

A major disadvantage with training exercises is that a radiographic image cannot be obtained during the exercise due to the radiation risk associated with real life radiological equipment. Furthermore, because known systems rely on pre-obtained images to show the patient positioning it does not provide positional feedback during the exercise as the patient or mannequin is manipulated or repositioned.

Another example of a radiological training simulation system is disclosed in United States Patent Application number US2009305215, which describes a mannequin equipped with sensors to generate x-ray images of the mannequin. A computer program generates pre-procedural x-ray images based on a desired simulation, and post-procedural x-ray images based on information obtained from the sensors both during and after the performance of a procedure. The computer program monitors sensor inputs during the course of the simulation including both force and positional sensor inputs.

Virtual radiology software simulation packages are known (www.shaderware.com). However, these packages do not actually modify the posture of a virtual model and they do not utilise a physical model or mannequin.

Furthermore, such packages do not allow for radiation dosimetry control but instead compute a dose-area product which is commonly used to indicate dose.

Aspects and embodiments of the present invention were devised with the foregoing in mind. For example, one or more of the problems associated with known training techniques may be addressed by providing a system and method which may allow for real time image simulation based on the actual position of an object or patient.

One or more embodiments of the present invention combine virtual, real-time construction of a computational phantom representing the human form and a simulation using the computational phantom, and a physical model, that is a mannequin representing the human form with imager model settings. This allows users to actually feel the physical presence of a patient in front of them and learn the physical limit of various radiographic positions and/or radiology procedures without the danger of exposure to radiation. The computational phantom may be, but not exclusively, a collection of image data. When the computational phantom is represented by a matrix of voxels it resembles a collection of cross-sectional images of a person. The phantom may also be represented by a series of meshes. In this context a mesh is a series of coordinates of points on a surface, arranged in a specific order such that a computer software module can interpret where the surface is or render the surface visually. Thus, in this context a computational phantom is a mathematical model of the human form or part thereof.

In addition one or more embodiments of the present invention include a relationship between image parameter settings (x-ray anode type and energy, filter, detector type, detector size, etc.) and the resultant image produced for medical examination.

Therefore, one or more embodiments of the present invention may allow users to become familiar with image quality, imaging systems and the effect of imaging system parameters on the image quality.

In one or more embodiments the mannequin may have the shape and the flexibility to be positioned by the users to any required radiographic position. Once the mannequin is positioned to the satisfaction of the user, the user can select the imager settings to obtain optimum images for that position.

One or more embodiments of the present invention may allow modelling of the morphology of certain diseases like tumours or other abnormalities. This will enable users to learn to identify different types of abnormalities, what imaging systems may be used to observe them and how an imaging system is optimised to observe them. It is also possible to compute the radiation dose, and users can learn to predict the optimum position for imaging with the least radiation dosage for a patient and also optimal shielding conditions for, for example infants and pregnant women.

In one or more embodiments Positron Emission Tomography (PET), Single Photon Emission Computed Tomography (SPECT) or other molecular imaging techniques can be simulated. The simulated image depends on a computer generated physiology of the patient, the amount of simulated radionuclide uptake and the postured computational phantom or simulation geometry. Users can set different radionuclide activity distributions where the distribution is a mathematical model of the radionuclide uptake in the organs of the posture phantom image and study the effects of different simulation settings on the generated simulated image.

One or more embodiments of the present invention can be integrated with Picture Archiving and Communications Systems (PACS) that are used in clinics and hospitals around the world. It is possible therefore to share the result of a particular simulation via a communication network such as the Internet or email.

Viewed from a first aspect the present invention provides a data processing apparatus for simulating radiological imaging of a physical object, the apparatus comprising: an object model generator configured to generate a data model, wherein the data model comprises data representative of the orientation of the physical object with respect to a frame of reference and simulated composition data; and an image simulator configured to perform a radiological simulation on the data model and generate a simulated radiological image of the physical object.

Viewed from a second aspect the present invention provides a method for simulating radiological imaging of a physical object, the method comprising: generating a data model, whereby the data model comprises data representative of the orientation of the physical object with respect to a frame of reference and simulated composition data; and performing a radiological simulation on the data model of the physical object in an image simulator and generating a simulated radiological image of the physical object.

Viewed from a third aspect the present invention provides a system for simulating radiological imaging of a physical object comprising the data processing apparatus according the first aspect, the system further comprising sensors to detect orientation of the physical object with respect to a frame of reference.

In one or more embodiments the computational phantom may be a data model and the computational phantom generator may be an object model generator.

In one or more embodiments the simulated composition data may be posture phantom image data and the image simulator may be a physics simulator.

In one or more embodiments the simulated radiological image is an image of simulated x-rays simulating exposure of a patient.

One or more embodiments of the invention may provide for the generation of real-time simulated radiographic images of an object. This eliminates the need for pre-obtained images to represent each possible position of the object. This may be achieved by generating a virtual model of the object based upon the object's position and generating simulated images by modelling the interaction of radiographic particles with the virtual model to produce simulated radiographic images. Furthermore, users can select between different radiological imaging procedures such as x-ray, PET and so on.

One or more embodiments of the present invention will now be described, by way of example only, with reference to the accompanying figures in which.

Figure 1:
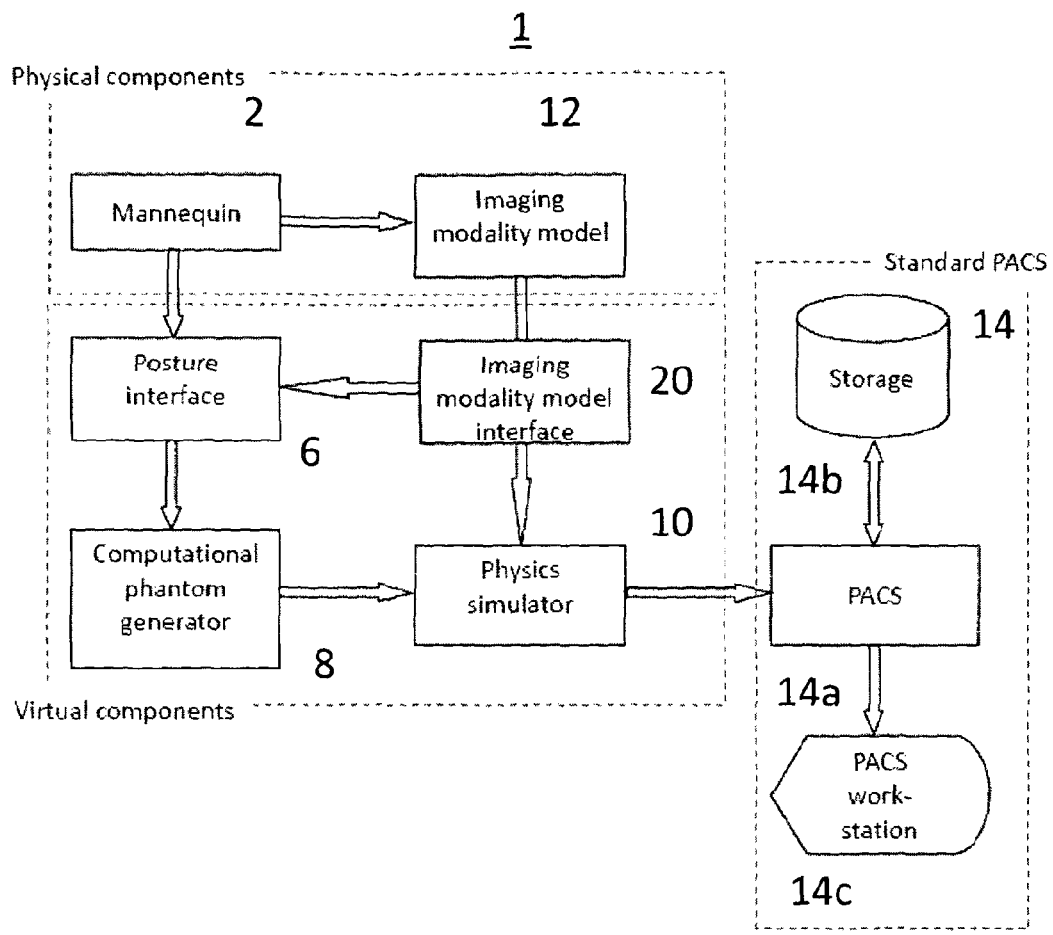
FIG. 1 is a block diagram illustrating components of a system in accordance with an embodiment of the present invention.

In overview FIG. 1 illustrates a system 1 for radiological simulation in accordance with an embodiment of the invention. The system 1 comprises an object to be modelled such as dummy or mannequin 2, a physical model 12 of a real life radiological imager, and a picture archiving and communication system (PACS) 14. The mannequin 2, the physical model 12 of a radiological imager and PACS 14 are physical components. The system 1 also comprises virtual components, namely: a posture interface 6; a computational phantom generator 8; a graphic user interface 20 for the imager 12; and a physics simulator 20. The virtual components are implemented in one or more data processing apparatus such as a computer workstation or general purpose computer.

The mannequin 2 can take the form of a human body. The mannequin 2 will have a realistic external shape with flexible joints to allow for manipulation and positioning of the mannequin. The mannequin 2 may also be a specific body part such as a hand, torso or leg. The mannequin 2 is composed of a light-weight skeleton structure and a poly-silicon skin, having for example, a realistic external shape of a human form. The mannequin is arranged to be manipulated by the user in the field of view the model of the imager 12. For example the mannequin may be arranged on a bed or couch in a prone position, or in a standing position.

The skeleton structure can be any appropriate lightweight material such as for example aluminium or carbon fibre. Anatomical landmarks, such as the clavicle, scapula, patella, and so forth, are attached to the skeleton and they can be felt by the user through the soft poly-silicon skin. The skeleton structure is connected by multiple-axis joints. The locations of these joints correspond to joints in a human skeleton, for example the cervix between the base of the skull and the spinal column, shoulders, elbows, wrists, hip joints, knees and ankles.

Rotation and position sensors 4 are placed at various positions on the mannequin 2 and provide angular, positional and rotational data representative of the orientation of the mannequin 2 relative to the physical model 12 of the radiological imager. The position sensors may be used to determine the position of the mannequin 2 with respect to the model of the radiological imager 12. Optionally or additionally, infrared (IR) sensors arranged on the model of the radiological imager 12 may also be used in conjunction with markers on the mannequin surface and external camera system to capture the position of the mannequin 2. This arrangement is a bio-mechanical tracker system commonly used in the computer game and movie industries, for example iPi Desktop Motion Capture™. The rotational sensors can be inserted inside the multi-axis joints of the mannequin. Since the dimensions of the mannequin are known and the position of each rotational sensor is known, the orientation of the joints with respect to each other and also the model of the radiological imager can be determined by the rotational sensors. The sensors are connected to the posture interface 6 via cables or a wireless communication system such as Bluetooth.

The physical model 12 of the radiological imager is a stylised mock-up of a typical imager which can be found in a hospital or clinic. The model 12 mimics the appearance and feel of a real-life imager. The shape and function of the model 12 of the radiological imager depend on the imaging simulation situation for example x-ray, CT, PET or SPECT and for the purposes of the present invention it is not essential that the imager 12 provides imaging capabilities, although it may do so. The model 12 not only provides a realistic physical model of the imaging equipment used in radiology, but also a frame of reference for the origin of imaging radiation in the simulated system.

The PACS 14 can include a PACS network 14a, data storage 14b, and one or more PACS workstations 14c connected to the PACS network 14a. The PACS workstations can include visual display units. Generated simulated images may for example conform to the DICOM (Digital Imaging and Communications in Medicine) standard so that integration with the PACS 14 is possible. This provides for standardised communication of images which may assist in the sharing of simulated results, review and/or assessment and in particular remote supervision and teaching.

The posture interface 6 is an interface between the sensors 4 of the mannequin 2 and the virtual components. Data from the sensors 4 can be fed to the posture interface 6 by radio frequency, cables, infrared and/or any other suitable communications medium. The posture interface 6 is implemented in software on a general purpose computer or workstation and is arranged to receive the positional and rotational data indicative of the orientation of the mannequin 2 from the rotation and position sensors.

The computational phantom generator 8 implemented in software on a general purpose computer or workstation constructs posture phantom image data of the mannequin based on data indicative of the orientation and position of the mannequin received from the posture interface 6. The posture phantom image data is constructed by the following steps, which comprise: mapping the skeleton joint positions of a reference phantom to the mannequin's joint information; deformation of a reference phantom skin mesh; interpolation of internal organ/tissue meshes and skin meshes of the skeleton; and voxelisation of the meshes and the association of voxels with the particular tissue characteristics of the meshes. In the context of the present application a voxel is a volume element, representing a value on a regular grid in three dimensional space. Therefore, for 3D simulations, volumetric images can be reconstructed.

Figure 2:
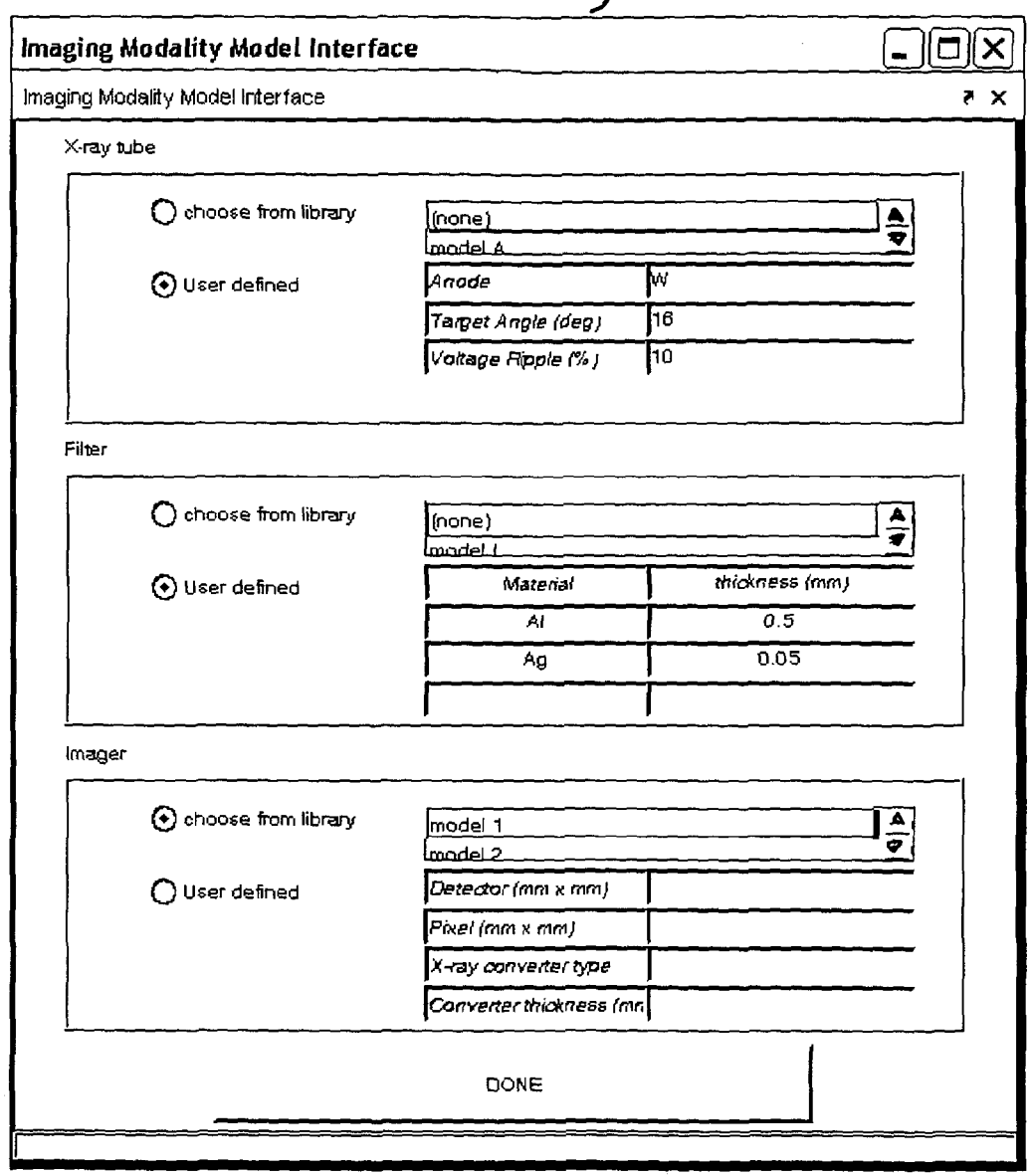
FIG. 2 is an example of a graphical user interface for setting a mode of operation the system in accordance with an embodiment of the invention.

The graphic user interface 20 (also known as an imaging modality model interface) as illustrated in FIG. 2 provides an input mechanism for a user to set imaging parameter data to be used in an imaging simulation. The user can define the imaging parameter data such as for example, filtration, tube voltage and tube current of the x-ray generator in the case of simulating x-ray based imaging procedures or type of radiopharmaceutical and its concentration in the case of simulating nuclear medicine procedures. For example, in a real life x-ray apparatus a filter is a piece of metal inserted at the bottom of an x-ray generator. For simulation of an x-ray process, in the modelled imager settings it is necessary to specify the material of the filter and the thickness of the material. Optionally or additionally predefined filter types may be selected based on commercially available filters. The imager interface 20 also allows users to choose other settings such as for example exposure settings kVp and tube filament current mAs. Voltage ripple, which is a fluctuation of x-ray tube voltage, can also be set using the imager interface 20 and the subsequent simulation will be more accurate if the voltage ripple is known and accounted for. CT generator characteristics can also be included on the interface because CT is x-ray based and therefore it is simply a rotating set of x-ray generator and imager. The principle of the CT is well known from G. N. Hounsfield, Computerized transverse axial scanning (tomography): Part 1. Description of system. British Journal of Radiology (1973) 46, 1016-1022. In a spiral CT simulation for example, the user is required to specify the x-ray source and detector characteristics as in other x-ray imaging methods. The pitch and the diameter of the spiral also need to be specified. The diameter of the spiral is determined by the distance between the x-ray focal spot and the detector. The pitch of the spiral, that is the distance that the patient has travelled after one rotation of a CT gantry, depends on the rotating speed of the gantry and the speed of the couch through the CT machine. After the CT signal is acquired, the 3D image is reconstructed using filtered back projection or other algebraic methods. PET and SPECT characteristics can also be included. PET and SPECT are based on radioisotope uptake in different types of tissue material. Therefore, PET and SPECT simulations start with the description of the radioisotope, its concentration and the physiological model.

Referring back to FIG. 1, the physics simulator 10 uses the posture phantom image data constructed by the computational phantom generator and simulates the path of modelled x-ray photons from a modelled x-ray generator through the posture phantom image data to their absorption in a modelled detector, thereby forming an image of the simulated x-rays to simulate exposure of a patient.

Figure 3:
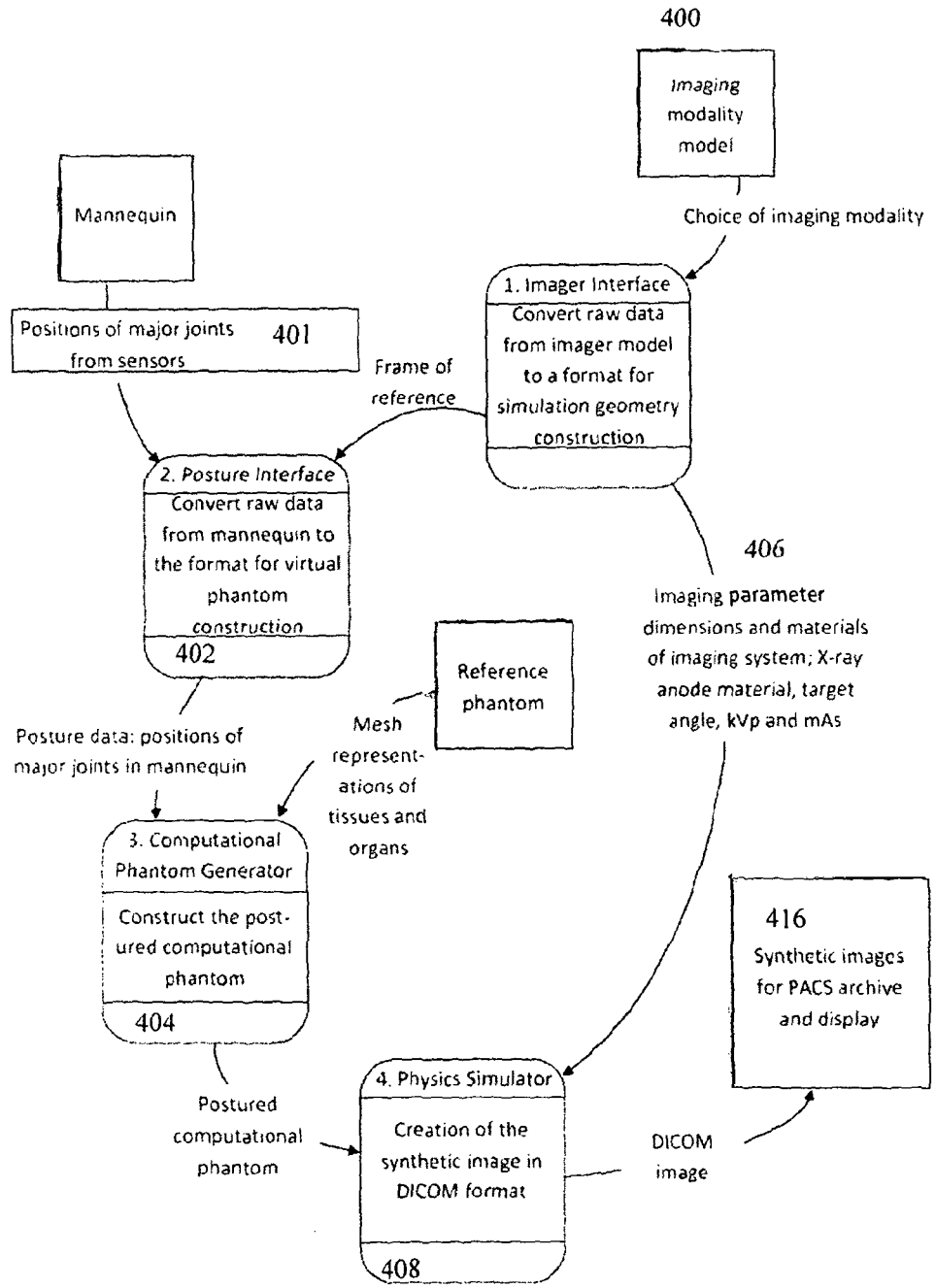
FIG. 3 is a schematic process flow control diagram illustrating the system data flow according to an embodiment of the invention.

In overview and referring to FIG. 3 the operation of the system 1 will now be described. Initially the user manipulates the mannequin 2 under the model of the imager 12 into a desired position for the desired radiological simulation. When the user is satisfied with the position of the mannequin they issue a command to read data and the posture interface 6 reads data (step 401) from the rotation/position sensors 4 of the mannequin 2 in response to the user command. The posture interface converts this data into a format suitable for construction of the posture phantom image data (step 402). This converted data is known as posture data. The posture interface 6 can generate a stylised visual representation of the position and orientation of the mannequin which may be displayed on a screen for the benefit of the user to enable the user to manipulate the mannequin into a suitable position for the desired radiological imaging process. Based on this data the posture interface 6 displays (on the display of the PACs 14c, or a separate display (not illustrated)) the mannequin's 2 posture and orientation relative to the physical model of the imager 12 in real time. This allows the user to obtain an initial image of the mannequin 2 prior to the desired radiological simulation process and allows the user to make adjustments to the position of the mannequin 2 relative to the imager 12. This enables the user to obtain the best possible simulated image for the desired simulation and is therefore an important training feature.

Automatically or in response to a user command, the posture interface 6 will then forward the posture data to the computational phantom generator 8 for construction of postured phantom image data (step 404). Following construction of the posture phantom image data, the posture phantom image data is made available to the physics simulator 10. The posture phantom image data can then undergo simulated interaction with virtual radiographic particles generated in software, to generate the simulated radiographic images (step 408). When the DICOM image is formed, it is passed to the PACS archive for storage and may be displayed on a display of the PACS work station (step 416).

To generate the simulated radiographic images the imaging parameter data as set by the user on the graphic user interface 20 (step 400) is also passed to the physics simulator 10 (step

406). As discussed, the settings include x-ray generator and detector characteristics and mimic the settings on a real life radiographic imager. The imager settings are made available to the physics simulator 10 so that physics simulator 10 can accurately simulate the interaction of virtual radiographic particles with the posture phantom image data. In this way a system according to an embodiment of the invention can accurately mimic a real life radiographic imaging process. The imaging parameter data also provides a frame of reference to the posture interface 6 to incorporate the posture phantom image data into the simulation process. The frame of reference allows the position of the imager to be mapped in relation to the position and orientation of the mannequin 2 based on the positional and orientation data from the sensors 4 with respect to the modelled imager.

Figure 4:
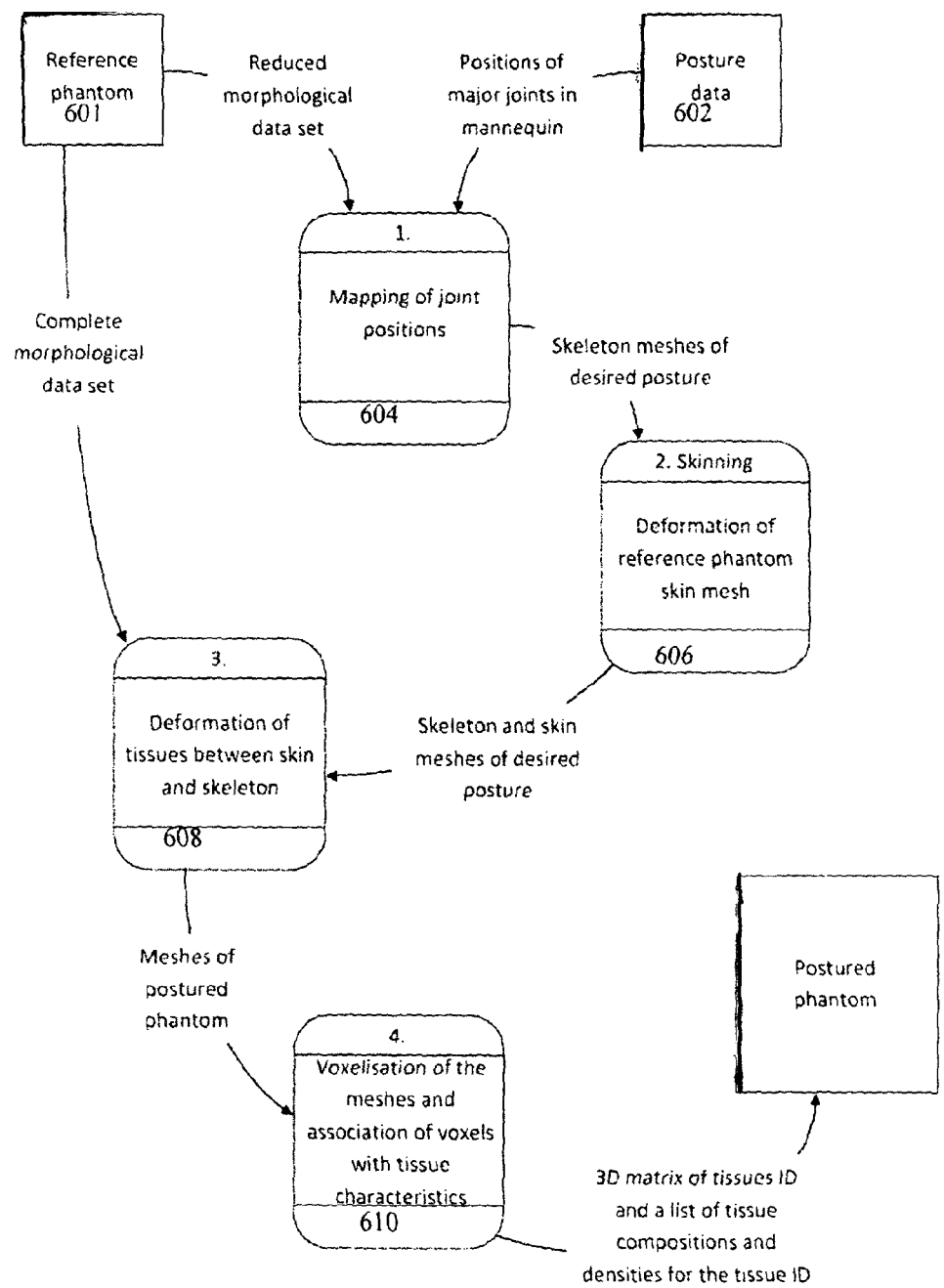
FIG. 4 is a schematic process flow control diagram illustrating the system data flow for generating posture phantom image data.

Referring now to FIG. 4 the function and operation of the computational phantom generator will now be described. The function of the computational phantom generator 8 is to generate posture phantom image data of the mannequin 2 for use in simulation of the radiological images by the physics simulator 10. The posture data from the posture interface 6 is passed (step 602) to the computational phantom generator 8. The posture data provides information on the position and orientation of joints in the mannequin 2 to represent the corresponding joints and features in the constructed posture phantom image data. In the computational phantom generator 8 the mannequin's 2 dimensions and joint positions are derived from a reference phantom so that the selected joints in mannequin 2 reflect those in the reference phantom. The reference phantom is selected so that it corresponds to the size of the mannequin so that the reference phantoms and mannequins are paired. For example an infant mannequin and will have a corresponding infant reference phantom. Construction of the reference phantom is discussed in more detail below with respect to FIG. 5.

Data from the reference phantom is modified based on the posture data from the mannequin 2 to construct the postured phantom. The postured phantom therefore is a modified version of the reference phantom, where the modification is based on the posture data from the posture interface 6. That is the position of the mannequin as determined by the sensors.

Using a reduced morphological data set obtained from the reference phantom (step 601) and the posture data obtained (step 602) from the posture interface 6, the computational phantom generator 8 maps (step 604) the posture of the mannequin to the reduced morphological data set. The positions of the mannequin joints have been determined from the posture interface 6 and therefore the end points of the skeletal bones of the finished computational phantom are known. If necessary, the end points of the skeletal bones of the reference phantom are moved to these positions. The reduced morphological data set has only skin and skeletal bones. It is relatively easy to modify the reference phantom into a postured phantom with skin and bones only. Using a reduced morphological data this speeds up the generation of the synthetic x-ray images compared to using a more complete morphological data set.

When generating posture phantom image data it is assumed that the skin of the mannequin is attached to the skeleton directly, therefore the skin mesh of the reference phantom is deformed dependent on the orientation of the mannequin.

A process known as skinning (step 606) is then used to create the posture phantom image data with bones and skin only. Skinning is a computer graphic technique used extensively in computer gaming and movie industries to produce an external shape of an animated character that moves with its skeleton. Following the skinning process the deformation of internal organs and tissues in the complete morphological data set is interpolated to follow the orientation of the mannequin to obtain a detailed posture phantom (step 608).

Figure 6:
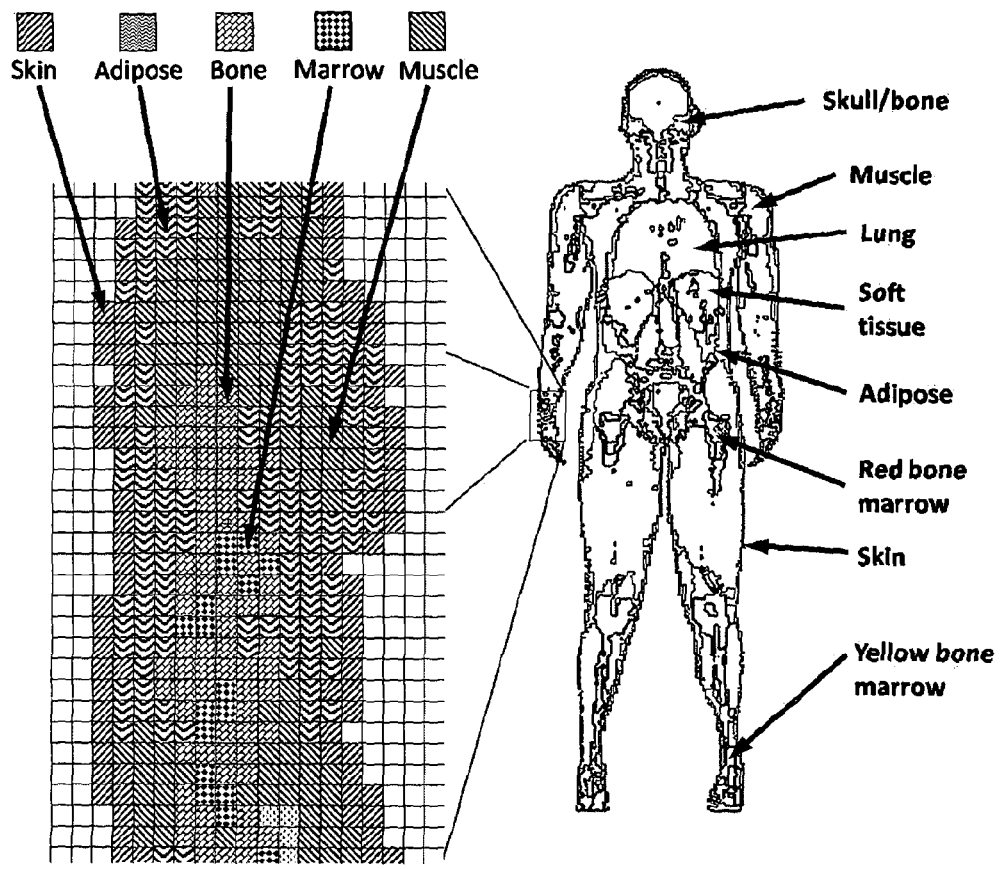
FIG. 6 illustrates a generated voxelised computational phantom of the human form.

The last step (step 610) in generation of the posture phantom image data is to generate a voxel based detailed posture phantom and to associate each voxel with elemental composition and density of the specific tissue type corresponding to that voxel to produce a voxelised image as shown in FIG. 6. FIG. 6 is an illustration of a generated voxelised computational phantom image of a human body. This voxelised phantom is the computational phantom image data required in the subsequent physics simulations involving the interaction of modelled radiation with the generated computational phantom image data.

Figure 5:
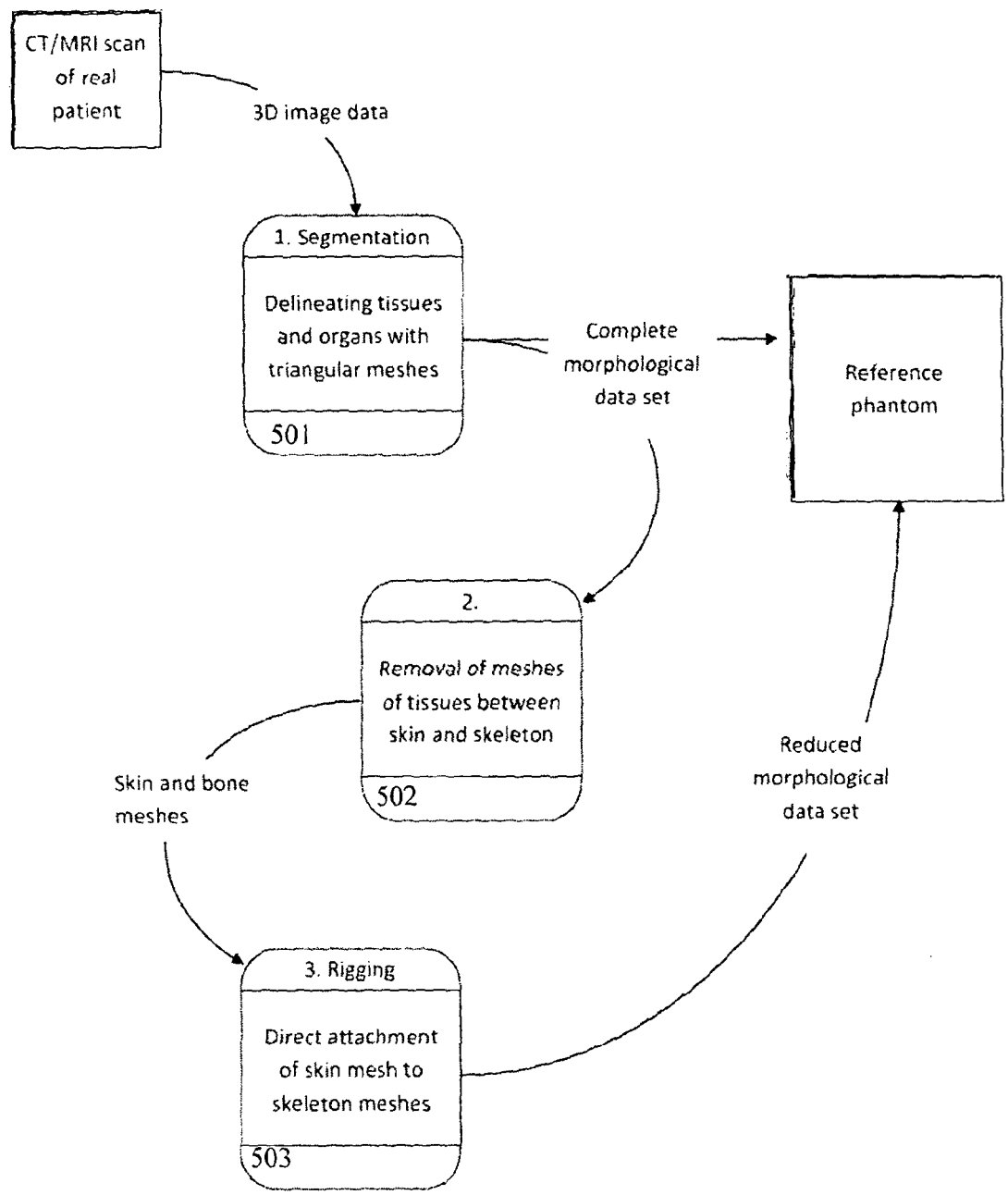
FIG. 5 is a schematic process flow control diagram illustrating the system data flow for generating a reference phantom.

The construction of the reference phantom will now be described. Referring to FIG. 5, the reference phantom is constructed where construction of the reference phantom is an intermediate step between receiving data from the posture interface and construction of the posture phantom image data. The reference phantom data is created from a CT/MRI scan of a real patient in a supine position. The CT or MR image is segmented (step 501) to delineate and define the major organs and tissues, including bones and skin, with triangular meshes. The triangular meshes together constitute a complete morphological data set of the reference phantom image data. The complete morphological data set is then processed to obtain a reduced morphological data set (steps 502 and 503) to remove all the organ and tissue meshes, except those for skeletal bones and skin, from the complete morphological data set.

At step 503, the skin mesh is attached to the skeletal bone meshes in a process known as rigging. This is a described in Ito et al (2009) "Robust generation of high-quality unstructured meshes on realistic biomedical geometry", *International Journal for Numerical Methods in Engineering*, vol. 65, pp. 943-973, the contents of which are incorporated herein by reference. The rigged meshes of skin and skeleton are the reduced morphological data set. The complete and the reduced data set together form the final reference phantom.

One advantage of using mannequins is that both real life models and generated models of different sizes, gender, ages and physiologies can be created. However, for reasons such as lack of patient consent, real patient CT/MRI images, as mentioned above, may not be available to create the reference phantom. In an alternative approach to the reference phantom generation discussed above, a Non-Uniform Rational B-Splines (NURBS) based image may be generated (see for example Lee et al "Hybrid computational phantoms of the male and female newborn patient: NURBS-based whole-body models," *Phys. Med. Biol.* 52 3309-3333 (2007)). NURBS generated images are based on mathematical representations of 3-D geometry that can accurately describe any shape from a simple 2-D line, circle, arc, or curve to the most complex 3-D organic free-form surface or solid. NURBS surfaces defining the model describe organ/tissue boundaries and segmentation is not necessary. The NURBS surfaces are converted directly into triangular meshes to obtain the complete morphological data set. Then a reduced data set is derived and rigging and skinning are applied as discussed above.

Figure 7:
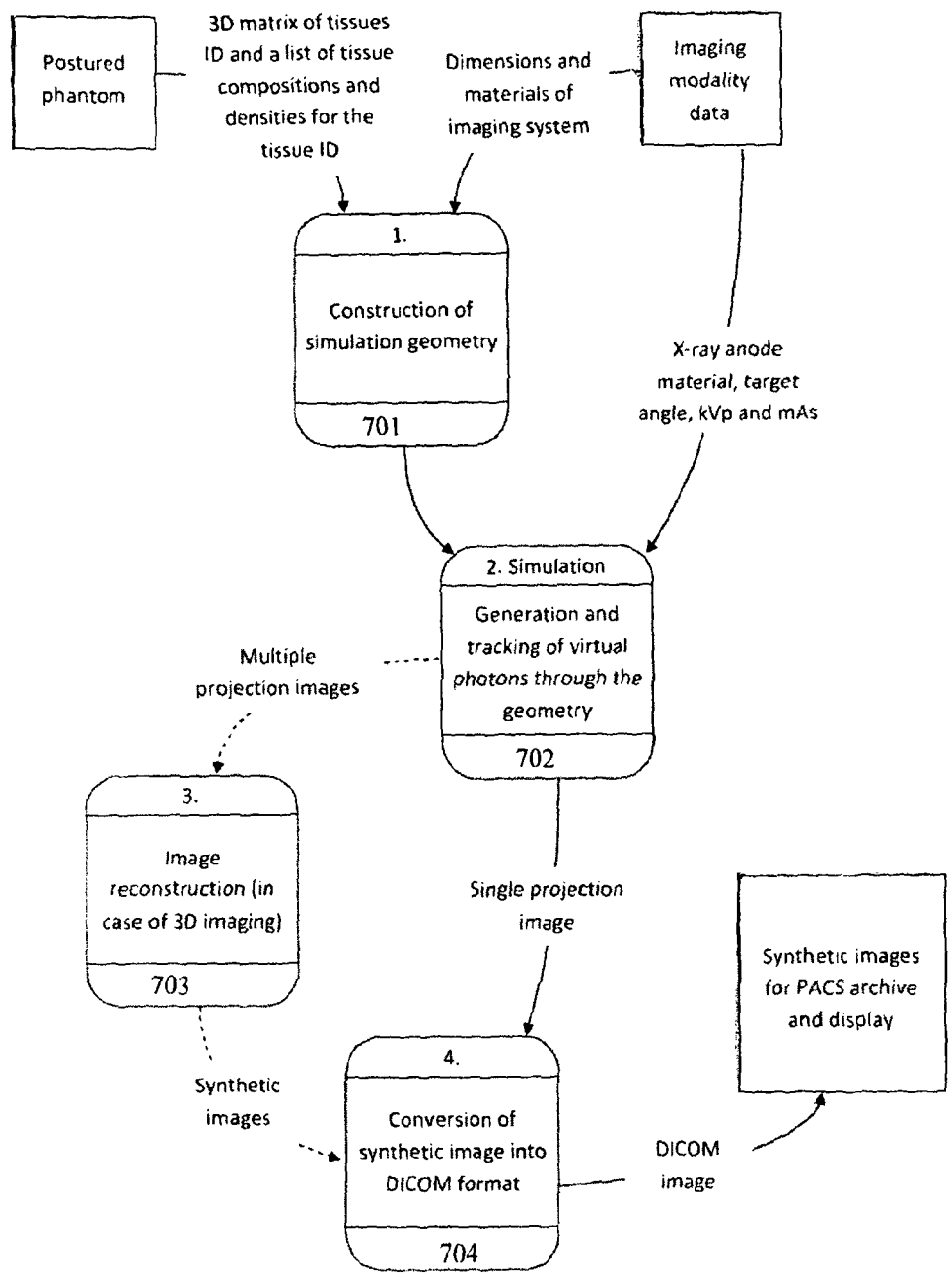
FIG. 7 is a schematic process flow control diagram of the physics simulator illustrating the data flow for generating simulated radiographic images.

Referring now to FIG. 7, and following generation of the computational phantom image data, the physics simulator 10 uses imaging parameter data as set by the user using the interface 20 to create the appropriate models of the radiation source and detectors. The physics simulator 10 generates and simulates virtual radiation particles through the imager and posture phantom image data.

The imaging parameter data is set by the user using the interface 20 of FIG. 2. For example, in x-ray based methods, including CT, users may choose the tube voltage (kVp), the tube current (mAs), the anode material, the target angle and the filter material. From these data, the energy spectrum and the angular distribution of the x-ray beam can be computed. Other imaging parameter data settings may include centering point, Source Surface Distance (SSD normally fixed at 100 cm or 80 cm) and collimation. The imaging parameter data will be transmitted via the graphic interface to position the source direction data and the position of the virtual phantom in the Monte Carlo simulation process, as discussed in more detail below.

The next step required from the user is to select the desired exposure parameters from imager model i.e. SSD, keV, mA and/or mAs. These data will also be fed to the Monte Carlo simulation process and thus, by selecting the x-ray exposure to run, the Monte Carlo simulation process will run using the data from the postured virtual phantom and the exposure data from the imager model. In nuclear medicine methods (PET and SPECT), the user may choose the type of radionuclide and its distribution in different tissues types. The type of radionuclide determines the gamma ray energy. The radionuclide's distribution in different tissues assumes a homogeneous uptake by each tissue. Therefore, the distribution specifies the percentage of the radionuclide in each tissue type. The emission of gamma rays is assumed to be isotropic at each source point. When the rays emerge from an organ or the body, the emission will no longer be isotropic. The tracking of the virtual photons in nuclear medicine is analogous to that of the x-ray based imaging modalities.

The virtual particle generation depends on the virtual radiation source. In the case of simulating x-ray based imaging modalities such as CT, chest x-ray, dental x-ray and so on, the anode-filter combinations are taken into account. The user chooses the tube voltage (kVp) and current (mAs). In the case of nuclear medicine based imaging modalities, the type of radioisotope, its activity and distribution in the body are specified by the user. Thus the physics simulator generates the virtual particles at energies, positions and directions relevant to the study.

As shown in FIG. 7, the physics simulator uses the posture phantom image data and the imager parameter data (in combination known as a simulation geometry) (step 701) to generate the simulated image. Each region of the computational phantom image data geometry is described by a combination of simple geometric surfaces. Together with the elemental composition and density of that region, the physics simulator (step 702) tracks the virtual photons from the virtual x-ray source through to absorption in a region or their escape from the simulation geometry. The virtual x-ray source data is constructed from the imager parameters from the imager model interface. In the case of 3D imaging modalities, multiple projection data or images are simulated and passed onto the image reconstruction module (step 703) to reconstruct the 3D synthetic image. In the case of 2D modalities, a single projection of a 2D synthetic image is simulated. The synthetic image is converted into DICOM format (step 704) for PACS archive or display.

The simulator then tracks the photons through the geometry using a combination of Monte Carlo and deterministic techniques such as ray tracing. For deterministic techniques, a pixel value in the imager is proportional to the sum of the linear attenuation coefficients along the path from the x-ray source to the pixel. Pixel values are computed one after another. In contrast, Monte Carlo simulation calculates the pixel value in a random fashion because the virtual photon arrives at a pixel randomly.

In the simulation process, the radiation physics relevant to diagnostic imaging are taken into account. They include photoelectric absorption, Rayleigh scattering and Compton scattering and position of the imager with respect to the sensor enabled mannequin. The particles are tracked until they are absorbed in the phantom, in the imager or they escape from the simulation geometry.

The simulated image is generated from the scoring of the virtual photons arriving at the imager. An image is a collection of the number of photons arriving at each detector pixel in real life. In a virtual simulation, the average number of photons arriving at each detector pixel is calculated. Thus, realistic simulated images can be generated that allow users to observe the effect of patient posture and their choice of radiation source and imager.

Figure 8:
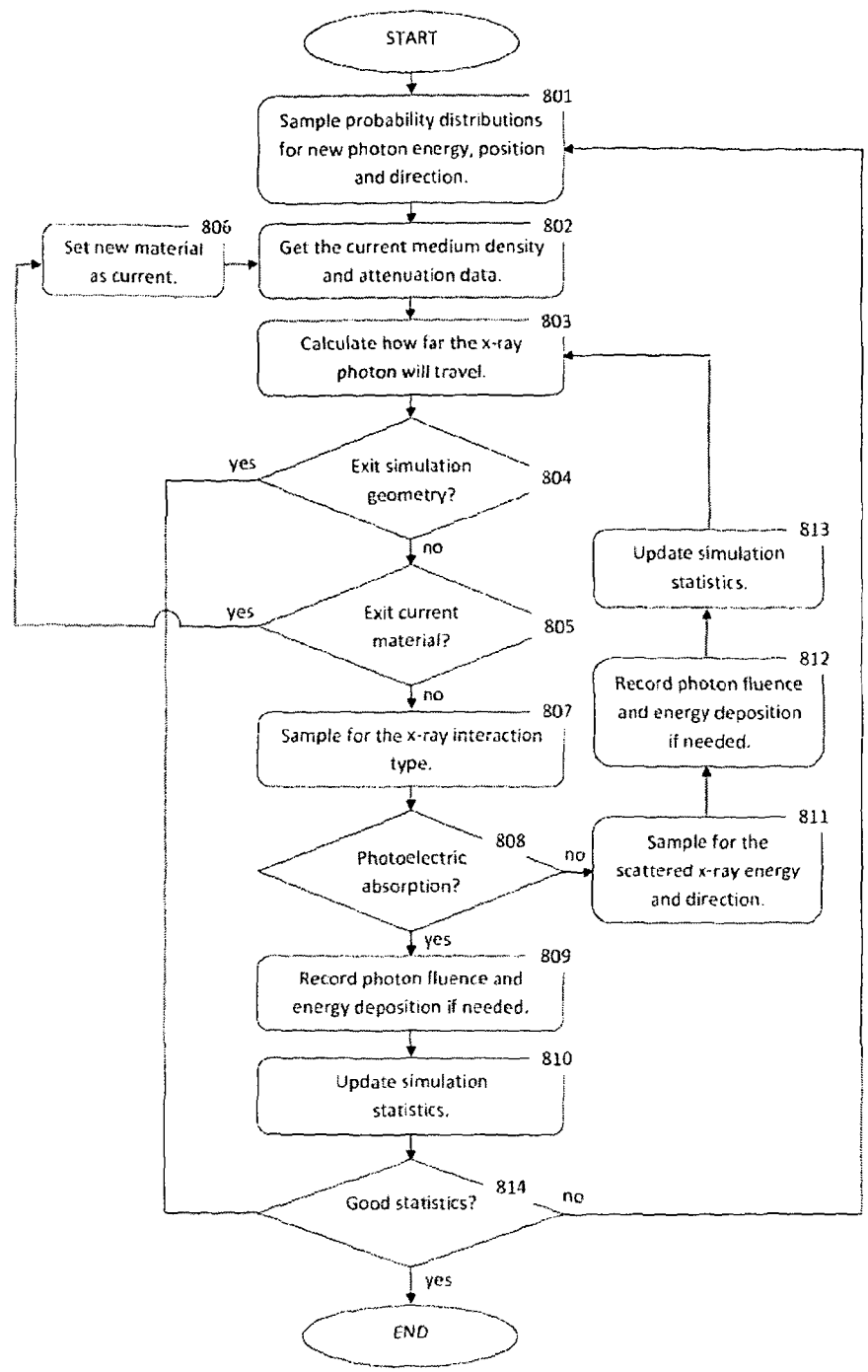
FIG. 8 is a schematic process flow control diagram illustrating a Monte Carlo simulation process.

The interactions of photons with matter are governed by probability distributions. These distributions are well-known and available from the literature. A Monte Carlo simulation, the steps of which are shown in FIG. 8, emulates these interactions by sampling the relevant probability distribution. At the start of the simulation of a photon from a known source, the photon's energy is sampled from the x-ray spectrum of the source. Its position and the direction are determined by the source location, dimension and material (step 801). The linear attenuation coefficient is a function of photon energy and the elemental composition and density of the medium (step 802). By sampling the probability distribution associated with the linear attenuation coefficient, the distance that the photon travels before coming into interaction is determined (step 803). If this distance brings the photon outside the current material and there is no material outside, the photon exits the simulation geometry and the program starts a new photon (step 804). If there is new material such as tissue or part of the imager, the new material will become the current material (step 806) and how far the photon will travel in the new material will be calculated from where the photon crosses the boundary (step 803) of the current material which may be a tissue boundary or a part of the imager. If the photon is still inside the current material, the interaction type will be determined by sampling the probability distribution of photoelectric absorption, Compton scattering and Rayleigh scattering (step 807). In the case of photoelectric absorption (step 808), the photon is terminated and its contribution to the simulation is tallied (step 809); simulation statistics are updated (step 810); a new photon will be generated and tracked (step 801). In case of Compton scattering, the new direction and energy of the photon are sampled from a Klein-Nishina cross-section (see for example Klein and Nishina, "Über die Streuung von Strahlung durch freie Elektronen nach der neuen relativistischen Quantendynamik von Dirac". *Z. F. Phys.* 52: 853-869 (1929); Kahn, "Applications of Monte Carlo," RM-1237-AEC The Rand Corporation (April 1956)) (step 811) which is the probability of a radiation particle undergoing a type of interaction with the medium. Klein-Nishina cross-section describes the probability of Compton scattering and again the simulation tally (step 812) and statistics (step 813) are updated. Then the tracking of the scattered photon continues with a calculation of how far it will travel in the current material (step 803).

In case of Rayleigh scattering, the scattered photon does not lose energy and the new direction is sampled from the cross-section of Rayleigh scattering (step 811). Then the simulation tally (step 812) and statistics (step 813) are updated and the scattered photon will be tracked as in the case of after Compton scattering (step 803). The simulation ends when the statistics satisfies some predefined criteria such as the number of simulated photons or the statistical fluctuation is below a required range (step 804).

Figure 9:
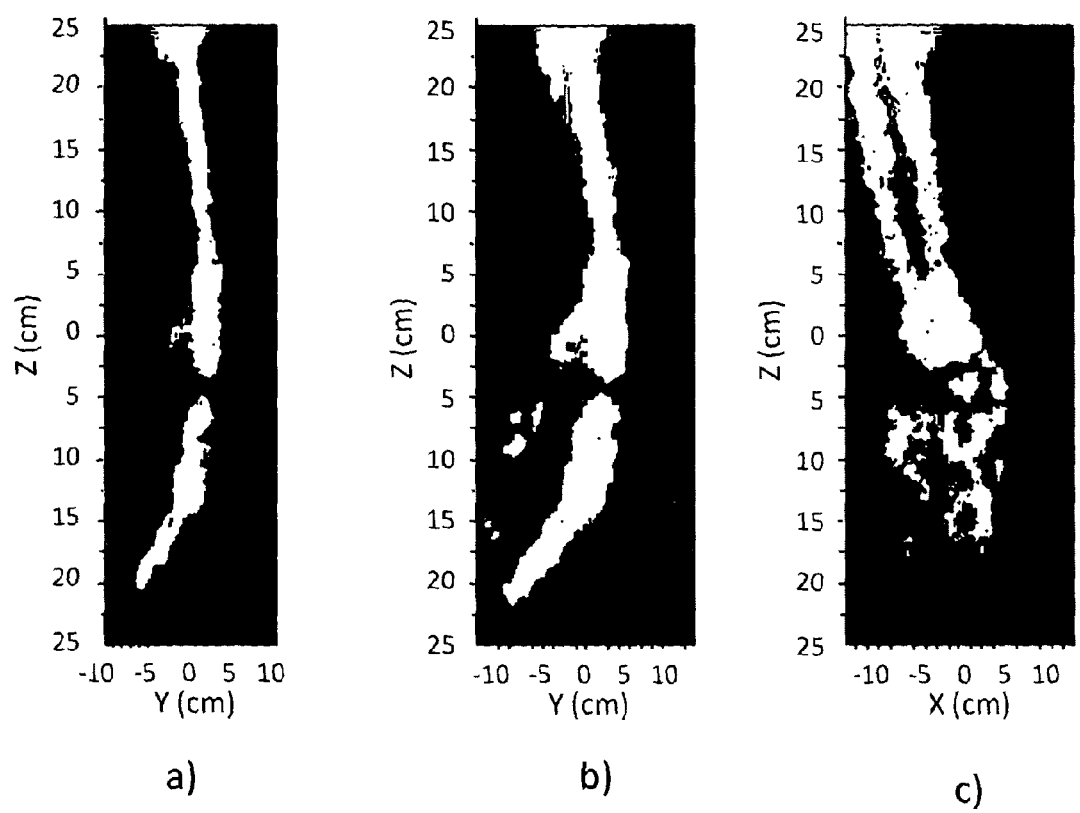
FIGS. 9a, 9b and 9c are simulated x-ray images of a human hand.

FIGS. 9(a) to 9(c) illustrate three simulated x-ray images with a low-resolution computational phantom to demonstrate the effect of different x-ray energies and postures of a hand. Observable anatomical features can differ in the images. Students can familiarize themselves with the choice of anode-filter combination, kVp and mAs settings in x-ray based imaging and radioisotopes and their activities in the cases of nuclear medicine.

Volumetric images (for example, CT and PET) are also reconstructed from the scores. All images are converted into DICOM format for storage and display by a PACS system.

Whilst foregoing aspects and embodiments of the invention have been described with respect to human medical imaging technology the invention may also find applications in veterinary practice.

Furthermore, embodiments of the invention may also find applications in engineering and/or material science. In engineering applications the mannequin or mannequin can be replaced by, for example, an engineering component, such as a turbine blade, aircraft wing, vehicle body part or integrated circuit. In this regard the invention may be utilised in training engineers or scientists to use radiological equipment for engineering applications.

Furthermore, embodiments of the present invention can be implemented by using a real life patient, or person acting as a patient. Here, as with the mannequin or mannequin the patient could be connected appropriate sensors to detect the position and orientation of the patient. Data from the sensors may then be made available to the posture interface and the computational phantom generated on the basis of the data from the sensors.

Particular aspects of embodiments of the invention are set out in the accompanying independent claims. Combinations of features from the dependent and/or independent claims may be combined as appropriate and not merely as set out in the claims.

Insofar as embodiments of the invention described above are implementable, at least in part, using a software-controlled programmable processing device such as a general purpose processor or special-purposes processor, digital signal processor, microprocessor, or other processing device, data processing apparatus or computer system it will be appreciated that a computer program for configuring a programmable device, apparatus or system to implement the foregoing described methods, apparatus and system is envisaged as an aspect of the present invention. The computer program may be embodied as any suitable type of code, such as source code, object code, compiled code, interpreted code, executable code, static code, dynamic code, and the like. The instructions may be implemented using any suitable high-level, low-level, object-oriented, visual, compiled and/or interpreted programming language, such as C, C++, Java, BASIC, Perl, Matlab, Pascal, Visual BASIC, JAVA, ActiveX, assembly language, machine code, and so forth. A skilled person would readily understand that term "computer" in its most general sense encompasses programmable devices such as referred to above, and data processing apparatus and computer systems.

Suitably, the computer program is stored on a carrier medium in machine readable form, for example the carrier medium may comprise memory, removable or non-removable media, erasable or non-erasable media, writeable or re-writeable media, digital or analogue media, hard disk, floppy disk, Compact Disk Read Only Memory (CD-ROM), Company Disk Recordable (CD-R), Compact Disk Rewriteable (CD-RW), optical disk, magnetic media, magneto-optical media, removable memory cards or disks, various types of Digital Versatile Disk (DVD) subscriber identify module, tape, cassette solid-state memory. The computer program may be supplied from a remote source embodied in the communications medium such as an electronic signal, radio frequency carrier wave or optical carrier waves. Such carrier media are also envisaged as aspects of the present invention.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

In view of the foregoing description it will be evident to a person skilled in the art that various modifications may be made within the scope of the invention.

The scope of the present disclosure includes any novel feature or combination of features disclosed therein either explicitly or implicitly or any generalisation thereof irrespective of whether or not it relates to the claimed invention or mitigate against any or all of the problems addressed by the present invention. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

The invention claimed is:

1. A data processing apparatus for simulating radiological imaging of a physical object, the apparatus comprising:
    an object model generator configured to:
        receive posture data, wherein the posture data comprises data representative of morphology of the physical object and simulated composition data; and
        generate a data model based at least in part on the posture data, wherein the data model comprises posture data representative of an orientation of the physical object with respect to a frame of reference and said simulated composition data; and an image simulator configured to perform a radiological simulation on the data model and generate a simulated radiological image of the physical object.

2. The data processing apparatus of claim 1, further comprising a data interface configured to convert the data representative of the orientation of the physical object into a format for generating the data model of the physical object.

3. The data processing apparatus of claim 2, wherein the object model generator is configured to receive the converted data from the data interface.

4. The data processing apparatus of claim 2, wherein the data interface is configured to generate a visual representation of the orientation physical object.

5. The data processing apparatus of claim 1, wherein the object model generator is configured to map the frame of reference on to the posture data representative of the orientation of the physical object to generate said data model.

6. The data processing apparatus of claim 1, further comprising a user interface configured to provide an input mechanism to define imaging parameters.

7. The data processing apparatus of claim 6, wherein the image simulator is configured to receive the imaging parameters to perform the radiological simulation.

8. The data processing apparatus of claim 6, wherein the imaging parameters comprise radiological source parameters and radiological detector parameters.

9. A method for simulating radiological imaging of a physical object, the method comprising:
receiving posture data, whereby the posture data comprises data representative of morphology of the physical object and simulated composition data;
generating a data model based at least in part on the posture data, whereby the data model comprises posture data representative of an orientation of the physical object with respect to a frame of reference and said simulated composition data; and
performing a radiological simulation on the data model of the physical object in an image simulator and generating a simulated radiological image of the physical object.

10. The method of claim 9, further comprising converting the posture data representative of the orientation of the physical object into a format for generating the data model of the physical object using a data interface.

11. The method of claim 10, whereby the data interface generates a visual representation of the orientation physical object.

12. The method of claim 9, further comprising mapping the frame of reference on to the posture data representative of the orientation of the physical object to generate said data model.

13. The method of claim 12, whereby the posture data comprises data representative of material type and material density.

14. The method of claim 9, further comprising defining imaging parameters.

15. The method of claim 14, whereby the image simulator receives the imaging parameters to perform the radiological simulation.

16. The method of claim 14, whereby the imaging parameters comprise radiological source parameters and radiological detector parameters.

17. The method of claim 9, whereby performing the radiological simulation is a statistical simulation process.

18. The method of claim 17, whereby the statistical simulation process is a Monte Carlo simulation.

19. A system for simulating radiological imaging of a physical object, the system comprising:
a data processing apparatus further comprising:
an object model generator configured to:
receive posture data, wherein the posture data comprises data representative of morphology of the physical object and simulated composition data; and
generate a data model based at least in part on the posture data, wherein the data model comprises posture data representative of an orientation of the physical object with respect to a frame of reference and said simulated composition data, and
an image simulator configured to perform a radiological simulation on the data model and generate a simulated radiological image of the physical object; and
sensors to detect orientation of the physical object with respect to a frame of reference.

20. The system of claim 19, wherein the sensors are positioned on the physical object.

21. The system of claim 19, wherein the physical object is a configurable or deformable mannequin.

22. The system of claim 19, wherein the sensors are positional and/or rotational sensors.

23. The system of claim 19, further comprising a physical model of a radiological imager.

24. The system of claim 23, wherein the physical model of the imager defines said frame of reference.

25. The system of claim 19, wherein the object model generator is configured to map the frame of reference on the posture data representative of the orientation of the physical object to generate said data model.

* * * * *